(12) United States Patent
Hogle (10) Patent No.: US 10,857,023 B1
(45) Date of Patent: Dec. 8, 2020

(54) NASAL DEVICE AND METHODS OF USE AND MANUFACTURE

(71) Applicant: Gregory Hogle, Denver, CO (US)

(72) Inventor: Gregory Hogle, Denver, CO (US)

(73) Assignee: Gregory A. Hogle, Denver, CO (US)

( * ) Notice: Subject to any disclaimer, the term of this patent is extended or adjusted under 35 U.S.C. 154(b) by 0 days.

(21) Appl. No.: 16/791,606

(22) Filed: Feb. 14, 2020

Related U.S. Application Data

(60) Provisional application No. 62/856,486, filed on Jun. 3, 2019.

(51) Int. Cl.
*A61F 5/08* (2006.01)
(52) U.S. Cl.
CPC ..................... *A61F 5/08* (2013.01)
(58) Field of Classification Search
CPC .. A61F 5/08; Y10T 24/1394; Y10T 24/44983; Y10T 24/44769
See application file for complete search history.

(56) References Cited

U.S. PATENT DOCUMENTS

| 4,592,357 | A | * | 6/1986 | Ersek | A61F 5/08 606/199 |
| 5,094,233 | A | * | 3/1992 | Brennan | A61F 5/08 602/17 |
| 5,350,396 | A | * | 9/1994 | Eliachar | A61F 5/08 602/17 |
| D414,872 | S | * | 10/1999 | Doyle | D24/128 |
| 5,983,898 | A | * | 11/1999 | Doyle | A61F 5/08 128/858 |
| D468,826 | S | * | 1/2003 | Doyle | D24/128 |
| D471,978 | S | * | 3/2003 | Doyle | D24/128 |
| 2005/0113850 | A1 | * | 5/2005 | Tagge | A61B 17/0469 606/151 |
| 2006/0260613 | A1 | * | 11/2006 | Pinter | A61F 5/08 128/206.11 |
| 2011/0230829 | A1 | * | 9/2011 | Fitzgerald | A61B 17/12 604/96.01 |

* cited by examiner

*Primary Examiner* — Tan-Uyen T Ho
*Assistant Examiner* — Rachel S Highland
(74) *Attorney, Agent, or Firm* — Kilpatrick Townsend & Stockton LLP; Kathy Warner; Clarke Weight (57) ABSTRACT

Devices and methods for creating a breathing passage and/or for maintaining a position of a septum. An exemplary device includes a base member, a first side member extending upward away from a first edge of the base member and being configured to contact a septum of a nasal cavity, and a second side member extending upward away from a second edge of the base member and being configured to contact a turbinate. The first and/or second side members are made of a flexible material. An exemplary method includes inserting a septum support into one side of a nasal cavity for creating a breathing passage, placing a first side member and a second side member of the septum support into contact with a septum and a turbinate, respectively. The first and second side members are biased away from one another such that pressure is applied to the septum.

20 Claims, 8 Drawing Sheets

NASAL DEVICE AND METHODS OF USE AND MANUFACTURE

CROSS-REFERENCE TO RELATED APPLICATIONS

This application claims the benefit of U.S. Provisional Patent Application No. 62/856,486, filed Jun. 3, 2019, entitled "NASAL DEVICE AND METHODS OF USE AND MANUFACTURE," which is incorporated by reference herein in its entirety for all purposes.

TECHNOLOGICAL FIELD

The subject invention relates generally to nasal devices and methods of using and manufacturing the same.

BACKGROUND

Various nasal surgeries may be performed to treat a variety of issues. For example, septoplasty may be performed to correct a deviated septum. To maintain the corrected, straight position of the septum during recovery, splints, such as a pair of Doyle splints, can be placed at either side of septum until the septum heals.

Another common nasal surgeries may include sinus surgery, which may be performed to open the pathways of the sinuses and clear blockages. During the sinus surgery, the middle turbinate, which tends to impede access to the sinuses, must be displaced in order for the surgeon to gain access to the sinus cavity. Techniques for displacing the middle turbinate include using a surgical instrument, such as a Freer elevator, to compress the middle turbinate towards the septum. Due to the middle turbinate's tendency to migrate, compression of the middle turbinate is often performed repeatedly during the surgery, causing collateral tissue damage.

BRIEF SUMMARY

The embodiments described herein provide nasal devices, such as septum support and/or nasal stents, having improved properties over conventional nasal devices. According to one aspect, a device for creating a breathing passage and/or for maintaining a position of a septum of a patient includes a base member, a first side member extending upward away from a first edge of the base member, and a second side member extending upward away from a second edge of the base member. The first side member is made of a flexible material and is configured to contact a septum of a nasal cavity. The second side member is also made of the flexible material and is configured to contact a turbinate. The base member, the first side member, and the second side member define a U shape with a substantially flat inner bottom and uneven sides. The second side member includes a length defined by a proximal edge of the second side member and a distal edge of the second side member such that the second side member is configured to extend longitudinally along and maintain contact with a portion of the turbinate while at least preventing blockage of sinuses or limiting contact with another turbinate above. The second side member includes a height defined by an upper edge of the second side member and the second edge of the base member such that the second side member is configured to extend vertically along and maintain contact with a portion of the turbinate while avoiding contact with another turbinate above. In some embodiments, the turbinate is an inferior turbinate, and the another turbinate above is a middle turbinate.

According to another aspect, a method for creating a breathing passage and/or for maintaining a position of a septum includes inserting a septum support into one side of a nasal cavity for creating a breathing passage. The method further includes placing a first side member of the septum support into contact with one side of the septum, and placing a second side member of the septum support into contact with a turbinate. The first side member and the second side member are biased away from one another such that pressure is applied to the one side of the septum by the first side member. The first side member and the second side member define an open end opposite to a base member of the septum support joining the first side member and the second side member.

BRIEF DESCRIPTION OF THE DRAWINGS

The present invention is described in conjunction with the appended figures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

Figure 1:
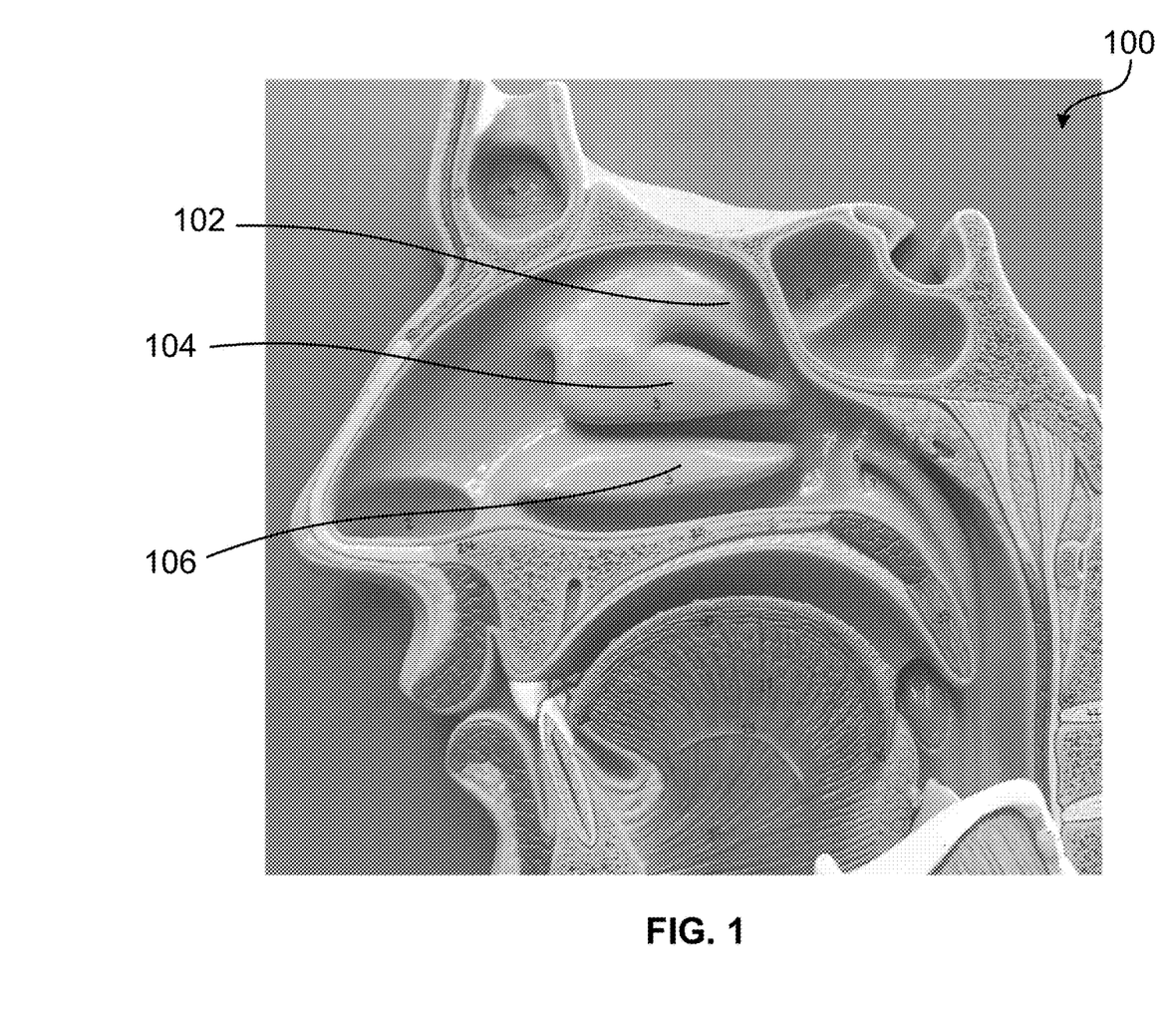
FIG. 1 illustrates a cross sectional view of part of the head along the parasagittal plane.

The nasal path is typically a curvy cavity or channel within the head. Several turbinates (a boney framework covered by soft spongy tissue) are positioned within the nasal cavity. FIG. 1 illustrates a cross sectional view 100 of part of the head along a parasagittal plane. The septum is removed from FIG. 1 to better illustrate the details inside the nasal cavity. There are most commonly three turbinates inside the nasal cavity: an upper or superior turbinate 102, a middle turbinate 104, and an inferior or lower turbinate 106. The turbinates cause turbulence (a physiologically important function) for air flow through the nose.

The septum, which separates the left and right airways of the nasal cavity, is hardly straight. Operational procedures, such as septoplasty, may be performed to correct a deviated septum. During recovery after an operational procedure, the septum needs to be supported so as to maintain and heal in a corrected, straight position.

Existing techniques for maintaining the corrected, straight position of the septum include placing splints, such as a pair of Doyle splints, on either side of the septum until the septum heals in the corrected, straight position. A Doyle splint includes a planar piece, one side of which is configured to contact one side of the septum and the other side of which is integrally formed with a curved piece to form an elongated half pipe. The planar pieces of a pair of the Doyle splints, disposed at either side of the septum, cooperate to maintain the straight position of the septum, and the half pipes of the Doyle splints operate as breathing passages for the patient.

One issue commonly encountered by patients with the Doyle splints is that the half pipes tend to get clogged given its elongated shape and fail to function as a breathing passage. About 50% of the surgeons avoid using the Doyle splints due to such blockage. Additionally, the curved piece extends along substantially the entire length of the planar piece. When the Doyle splint is placed into the nasal cavity, the posterior aspect of the curved half pipe component compresses the middle turbinate 104 laterally. The term "laterally" means outward from the midline of the body, and the term "lateral" is used herein to describe a position that is further from the midline of the body. If sinus surgery has been performed in combination with septoplasty, then post-operative healing for the sinus surgery component may be compromised by the half pipe component causing lateralizing compression of the middle turbinate 104. This problem is another reason that surgeons choose not to insert the Doyle splints.

In some aspects, the present technology described herein provides a septum support configured to create a breathing passage and/or to maintain the septum in an upright and/or straight position while avoiding at least some or all of the issues discussed above. In some embodiments, a pair of the septum supports as described herein may be used to support the septum and to provide a breathing passage. Each septum support may include a base member, a first side member, and a second side member that collectively define a U-shaped channel or a trough with uneven sides. As compared to the half-pipe design of the Doyle splint, the open design of the septum support provides a breathing passage for the patient that is less likely to be blocked, and any accumulation can be easily rinsed out.

The first side member may be characterized by a height and a length that substantially corresponds to the height and the length of the septum, respectively, such that the first side member supports the entire septum vertically and longitudinally. The second side member may be characterized by a height less than that of the first side member such that it contacts the inferior or lower turbinate while limiting or avoiding contact with the middle turbinate. Additionally, the second side member includes a length that is less than the length of the first side member such that the second side member does not extend as far back into the nasal cavity as the first side member, not only avoiding contact with the middle turbinate, but also preventing blockage or irritation to the sinuses.

The second side further includes a curved portion that defines a concave surface that substantially conforms to the curvature or contour of the inferior or lower turbinate. As compared to the conventional Doyle splint which contacts the surfaces of one or more turbinates with the convex surface of its half pipe, the concave surface of the second side member of the present technology distributes the pressure imparted on the inferior or lower turbinate in a more uniform manner, and thus is more comfortable for the patient.

Further, the base member has a planar design, which provides a greater surface area for the septum support to rest on the floor of the nasal cavity. In contrast, the Doyle splint rests on the bottom edge of its planar piece when placed in the nasal cavity, which can cause discomfort and/or irritation to the nose. The planar design of the base member of the nasal support described herein significantly reduces or limits such discomfort and/or irritation.

In further aspects, the present technology provides a nasal stent that is positionable within the nose to open up an airway or fluid passage within the nose. In some embodiments, a single nasal stent or a pair of nasal stents as described herein may be used to create access for a surgeon to reach sinuses during operational procedures. Specifically, the nasal stent described herein includes two side members extending upward from a base member and biased away from each other. One of the side members is configured to press laterally against a lateral nasal wall, while the other one of the side members is positionable on a lateral side of one of the turbinates and is able to press against that turbinate medially toward the septum and to hold that turbinate in a displaced position against the septum. The term "medially" means inward toward the midline of the body, such as the septum, and the term "medial" is used herein to describe a position that is closer to the midline of the body. The displaced turbinate increases the viewing space within the nasal cavity and provides access to portions of the sinus that are typically blocked or covered by the turbinate.

Constant maintenance of the medialized turbinate position allows for a continuous, maximized view of the sinus cavity. By maximizing the viewing area, the surgeon has improved access to the sinuses and improved efficiency while minimizing the likelihood for a surgical complication. Moreover, the nasal stent minimizes trauma to the turbinate caused by repeatedly repositioning the turbinate medially with an instrument, such as a Freer elevator, which can cause permanent alteration of the turbinate, which in turn can affect the turbinate's function. In contrast, the stent described herein is able to displace the turbinate, such as the middle turbinate, with minimization of trauma. Further, by eliminating the time requirement for repeated turbinate compressions, the stent described herein improves efficiency of the surgeon and shortens the operation time for the patient. The nasal stent may be sufficiently flexible to enable easy insertion within the nose, yet sufficiently stiff or rigid to maintain the medial displacement of the middle turbinate.

Figure 2A:
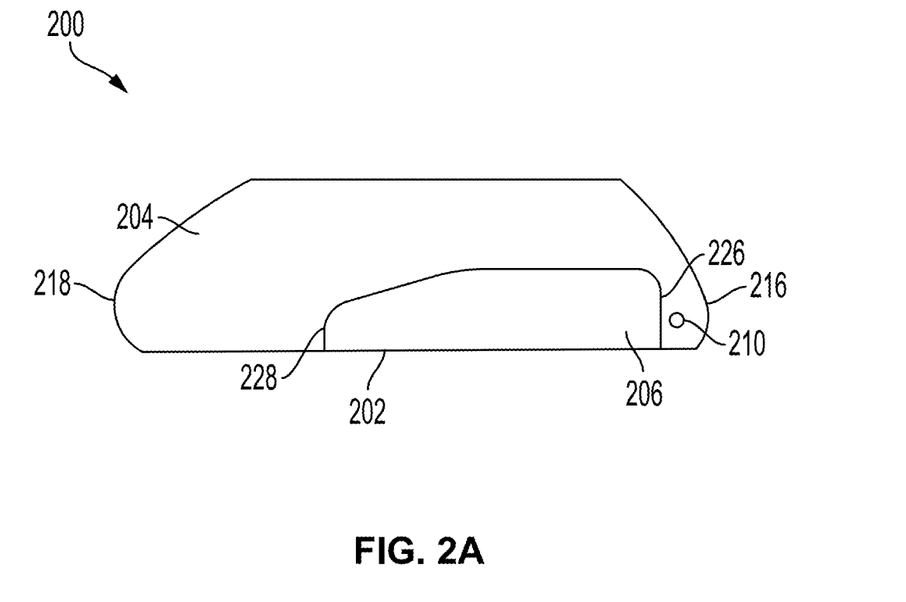
FIG. 2A illustrates a side or lateral view of an embodiment of a septum support that is configured for creating a breathing passage and/or for maintaining a position of a septum of a patient.
Figure 2B:
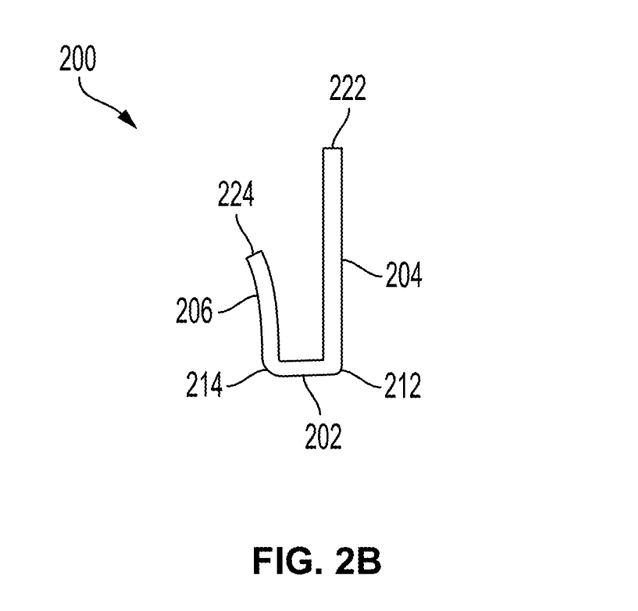
FIG. 2B illustrates a front or anterior view of the septum support of FIG. 2A.

FIG. 2A illustrates a side or lateral view of a septum support 200 that is configured for creating a breathing passage and/or for maintaining a position of a septum of a patient. FIG. 2B illustrates a front or anterior view of the septum support 200. The septum support 200 illustrated in FIGS. 2A and 2B is a right septum support that is configured to be placed or inserted into the right side of the nasal cavity.

As will be described in more detail below, in operation, the right septum support operates together with a left septum support that is constructed similarly to the right septum support but is configured to be placed or inserted into the left side of the nasal cavity to maintain the septum in an upright or straight position and/or to create a breathing passage for the patient.

As shown in FIGS. 2A and 2B, the septum support 200 includes a base member 202, a first side member 204 extending upward away from a first edge 212 of the base member 202, and a second side member 206 extending upward away from a second edge 214 of the base member 202. The base member 202, the first side member 204, and the second side member 206 collectively define a U-shaped channel or a trough with uneven sides. In other words, the first side member 204 and the second side member 206 define an open end opposite to the base member 202 joining the first side member 204 and the second side member 206. As compared to the half-pipe design of a Doyle splint, the open design of the septum support 200 provides a breathing passage for the patient that is less likely to be blocked, and any accumulation can be easily rinsed out with water, saline or other solutions.

The base member 202 is substantially planar and is configured to rest on a bottom or floor of the nasal cavity of the patient. The first and second edges 212, 214 of the base member 202 define a width of the base member 202 that helps to maintain the orientation and/or position of the septum support 200 in the nasal cavity, including maintaining a generally upright position of the first side member 204 so as to keep the septum straight. In some embodiments, the width of the base member 202 ranges between about 3 mm and about 8 mm, between about 3 mm and about 7 mm, or between about 4 mm and about 6 mm, such as about 5 mm. The width of the base member 202 may be consistent throughout its longitudinal extension. The planar design of the base member 202 provides a greater surface area for the septum support 200 to rest on the floor of the nasal cavity as compared to the existing technologies. For example, in a conventional Doyle splint, only the bottom edge of the planar piece of the Doyle splint may rest on the floor of the nasal cavity, which can cause discomfort and/or irritation to the nose. The planar base member 202 of the present technology significantly reduces or limits such discomfort and/or irritation.

As will be described in more detail below, the first side member 204 and the second side member 206 have different lengths. In some embodiments, the base member 202 may include a length that is substantially the same as the length of the first side member 204. In other words, the base member 202 and the first side member 204 may be coextensive along the longitudinal dimension of the septum support 200. In some embodiments, the base member 202 may include a length that is substantially the same as the length of the second side member 206. That is, the base member 202 and the second side member 206 may be coextensive along the longitudinal dimension of the septum support 200. In some embodiments, the base member 202 may include tapered end portion or portions that expand between the longitudinal ends of the first side member 204 and the second side member 206.

As mentioned above, the septum support 200 illustrated in FIGS. 2A and 2B is a right septum support configured to be placed in the right side of the nasal cavity. When the septum support 200 is inserted into the right side of the nasal cavity, the first side member 204 is configured to contact the right side of the septum, and the second side member 206 is configured to contact a turbinate, such as the inferior or lower turbinate 106, on the right lateral wall of the nasal cavity.

The first side member 204 is substantially planar so as to maintain the septum in a substantially upright or straight position. The first side member 204 includes a length defined by a proximal edge 216 and a distal edge 218 of the first side member 204. The length of the first side member 204 may substantially correspond to the length of the septum such that the first side member 204 supports substantially the entire septum along the longitudinal extension of the septum. In some embodiments, the length of the first side member 204 ranges between about 65 mm and about 75 mm, or between about 65 mm and about 70 mm, such as about 68 mm. The first side member 204 includes a height defined by an upper edge 222 of the first side member 204 and the first edge 212 of the base member 202 such that the first side member 204 supports substantially the entire septum vertically. In some embodiments, the height of the first side member 204 ranges between about 15 mm and about 25 mm, between about 17 mm and about 23 mm, or between about 19 mm and about 23 mm, such as about 21 mm. The upper edge 222 of the first side member 204 may be substantially straight while the proximal and distal edges 216, 218 may be curved so as to form tapered proximal and distal ends of the septum support 200 to facilitate the insertion and removal of the septum support 200 into and out of the nasal cavity.

In some embodiments, the first side member 204 includes an aperture or suture hole 210 near the proximal edge 216 of the first side member 204 so that the first side member 204 can be sutured to the septum near the columella, which is the soft tissue and skin overlying the anterior edge of the septum, through the suture hole 210 to further secure the position of the septum support 200 inside the nasal cavity. In some embodiments, the first side member 204 may be adhered to the septum support 200 using adhesive or glue as an alternative to or in addition to suturing.

As mentioned above, the second side member 206 is configured to contact a turbinate on the right lateral wall of the nasal cavity. More specifically, the second side member 206 is configured to contact the inferior or lower turbinate 106 while limiting or avoiding contact with the middle turbinate 104. Thus, the second side member 206 includes a height as defined by an upper edge 224 of the second side member 206 and the second edge 214 of the base member 202 that is less than the height of the first side member 204 so as to limit or avoid contact with the middle turbinate 104. Additionally, the second side member 206 includes a length as defined by a proximal edge 226 and a distal edge 228 of the second side member 206 that is less than the length of the first side member 204 such that the second side member 206 does not extend as far back into the nasal cavity as the first side member 204 so as to limit or avoid contact with the middle turbinate 104, as well as to limit or prevent blockage or irritation to the sinuses. In some embodiments, the height of the second side member 206 ranges between about 5 mm and about 15 mm, or between about 8 mm and about 13 mm, such as about 11 mm. In some embodiments, the length of the second side member 206 ranges between about 35 mm and about 45 mm, or between about 37 mm and about 42 mm, such as about 39 mm.

With reference to FIG. 2B, different from the planar configuration of the first side member 204, the second side member 206 includes a curved portion with a convex surface facing the first side member 204 such that the first side member 204 and the second side member 206 diverge from the base member 202. Thus, the distance between the first side member 204 and the second side member 206 at a vertical position above the base member 202 is greater than the distance between the first side member 204 and the second side member 206 at the base member 202 or the width of the base member 202.

The curved portion also forms a concave surface that substantially conforms to the curvature or contour of the inferior or lower turbinate 106. As compared to the conventional Doyle splint which contacts the surfaces of one or more turbinates with the convex surface of its half pipe, the concave surface of the second side member 206 of the present technology distributes the pressure imparted on the inferior or lower turbinate 106 in a more uniform manner, and thus is more comfortable for the patient.

The septum support 200 is configured so that the first side member 204 and the second side member 206 are biased away from one another. The biased configuration results in the first side member 204 contacting and/or pressing against the septum and the second side member 206 contacting and/or pressing against the inferior or lower turbinate 106. In some embodiments, the septum support 200 is resilient such that the first side member 204 and the second side member 206 can be pinched together to reduce the distance between the first side member 204 and the second side member 206 to facilitate insertion of the septum support 200 into the nasal cavity. Once placed into the nasal cavity, the resiliency of the septum support 200 restores the distance between the first side member 204 and the second side member 206 at least to the extent such that the first side member 204 and the second side member 206 are biased away from each other to contact and/or press against the septum and the inferior or lower turbinate 106, respectively. Such biased configuration allows the first side member 204 to apply pressure to one side of the septum. When operating in pair, the left and right septum supports apply pressure to both sides of the septum, and the planar configuration of the respective first side members maintain a straight and/or upright position of the septum.

To achieve the desired resiliency and the biased configuration, in some embodiments, the first side member 204 and/or the second side member 206 are made of a resilient and/or flexible material, such as a shape memory material including a shape memory alloy, a superelastic material, e.g., a superelastic alloy, an elastic material, a polymeric material, or other resilient and/or flexible material. In some embodiments, the first side member 204 and/or the second side member 206 are made of Nitinol. In some embodiments, the first side member 204 and/or the second side member 206 are made of silicone. The resiliency of the material forming the first side member 204 and/or the second side member 206 restores the shapes of and/or distance between the first side member 204 and the second side member 206, and biases the first side member 204 and/or the second side member 206 from each other when inserted into the nasal cavity.

Figure 2C:
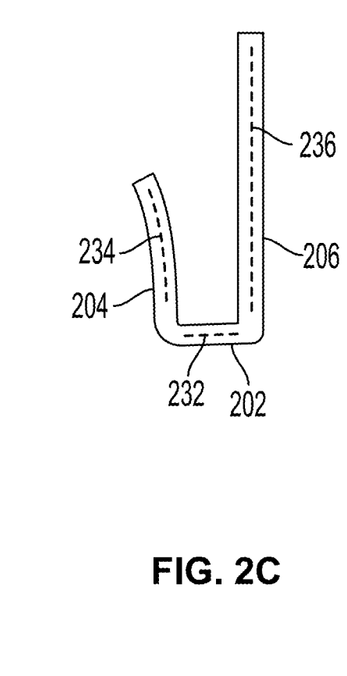
FIG. 2C illustrates a front or anterior view of another embodiment of a septum support.

In some embodiments, at least one of the first side member 204 and/or the second side member 206 includes a reinforcing member, such as reinforcing member 234 and/or reinforcing member 236 shown in FIG. 2C, which may be at least partially embedded in the first side member 204 and/or the second side member 206 and may be configured to bias the first side member 204 and the second side member 206 apart.

In some embodiments, the base member 202 is made of the same material as the first side member 204 and/or the second side member 206, while in other embodiments, the base member 202 is made of a material different from that used for making the first side member 204 and/or the second side member 206. In some embodiments, the base member 202 is made of a resilient and/or flexible material, such as a shape memory material including a shape memory alloy, a superelastic material, e.g., a superelastic alloy, an elastic material, a polymeric material, or other resilient and/or flexible material. In some embodiments, the base member 202 is made of Nitinol. In some embodiments, the base member 202 is made of silicone.

In some embodiments, the base member 202 is more rigid than the first side member 204 and the second side member 206 so as to maintain the distance between the first side member 204 and the second side member 206 and support the septum support 200 in a substantially upright position inside the nasal cavity. Yet, the base member 202 may still be flexible enough to allow bending and/or folding to facilitate insertion of the septum support 200 into the nasal cavity. In some embodiments, the base member 202 may be made of a material that is more rigid than the material used for making the first side member 204 and/or the second side member 206. In some embodiments, the base member 202 may include a greater thickness than that of the first side member 204 and/or the second side member 206 to achieve desired rigidity. For example, the first side member 204 and/or the second side member 206 may include a thickness that is less than or about 1 mm, less than or about 0.8 mm, less than or about 0.6 mm, or less, whereas the base member 202 may include a thickness that is greater than or about 1 mm, greater than or about 1.2 mm, greater than or about 1.4 mm, or greater.

In some embodiments, the base member 202 is less rigid than the first side member 204 and/or the second side member 206 such that the base member 202 can be easily bended and/or folded to facilitate insertion of the septum support 200 into the nasal cavity. Once the septum support 200 is placed inside the nasal cavity, a reinforcing member may be positioned between the first side member 204 and the second side member 206 and rest on the base member 202 to maintain the planar configuration of the base member 202 inside the nasal cavity.

In some embodiments, whether the base member 202 is less rigid or more rigid, or has a similar rigidity to that of the first side member 204 and/or the second side member 206, a reinforcing member may be nonetheless included. In some embodiments, a reinforcing member, such as reinforcing member 232 shown in FIG. 2C, may be embedded in the base member 202. Although FIG. 2C illustrates three separate, individual reinforcing members 232, 234, 236, the reinforcing members 232, 234, 236 may be formed as one single, continuous piece embedded in the base member 202, the first side member 204, and the second side member 206.

Figure 2D:
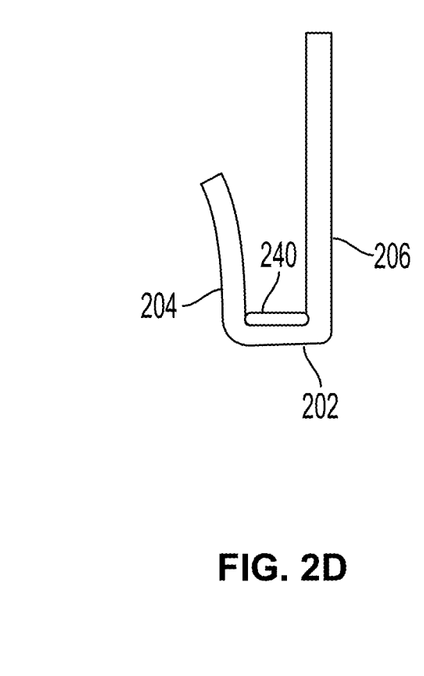
FIG. 2D illustrates a septum support having a reinforcing member positioned at a first location.

In some embodiments, a reinforcing member, such as reinforcing member 240 shown in FIG. 2D, may be placed between the first side member 204 and the second side member 206 to maintain the planar configuration of the base member 202 inside the nasal cavity. In some embodiments, the reinforcing member 240 may also rest on the base member 202, which may support the reinforcing member 240.

Figure 2E:
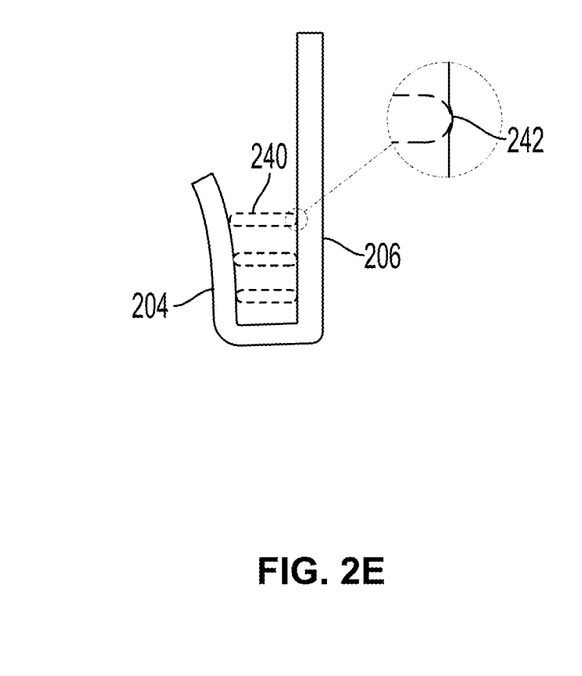
FIG. 2E illustrates a septum support having a reinforcing member positioned at various locations.

In some embodiments, the reinforcing member 240 may be positioned between the first side member 204 and the second side member 206 and above the base member 202, such as shown in FIG. 2E. Positioning the reinforcing member 240 above the base member 202 and between the first side member 204 and the second side member 206 biases the first side member 204 and the second side member 206 away from each other. The first side member 204 and the second side member 206 may include grooves, such as groove 242 shown in the inset of FIG. 2E, that are configured to engage the reinforcing member 240. This may allow the reinforcing member 240 to be placed at various heights (as indicated in dashed lines in FIG. 2E) to adjust the distance between the first side member 204 and the second side member 206 to better fit the septum support to different patients. In some embodiments, a reinforcing member of a common size may be placed at various heights, while in other embodiments, reinforcing members of various sizes may be selected and placed at various heights to accommodate different patients or for other considerations.

The reinforcing member 240 may be made of the same material as the base member 202, the first side member 204, and/or the second side member 206, or may be made of a different material. In some embodiments, the reinforcing member 240 is made of a resilient and/or flexible material, such as a shape memory material including a shape memory alloy, a superelastic material, e.g., a superelastic alloy, an elastic material, a polymeric material, or other resilient and/or flexible material. In some embodiments, the reinforcing member is made of Nitinol. In some embodiments, the reinforcing member 240 is made of silicone.

Although FIGS. 2A and 2B illustrate that the base member 202, the first side member 204, and the second side member 206 are each made of a continuous piece of material, one or more of the base member 202, the first side member 204, and/or the second side member 206 may be made of a mesh or wire material. The septum support 200 may be made using any suitable manufacturing methods or techniques depending on the material(s) used to form the septum support 200. For example, the septum support 200 may be molded as one integral piece into the desired shape and configuration. In some embodiments, the molding material may be molded around one or more reinforcing members, such as reinforcing members 232, 234, 236 described herein, to form the septum support 200. In some embodiments, the septum support 200 may be made by scoring and/or folding or bending a piece of resilient material into the desired shape and configuration.

Figure 3:
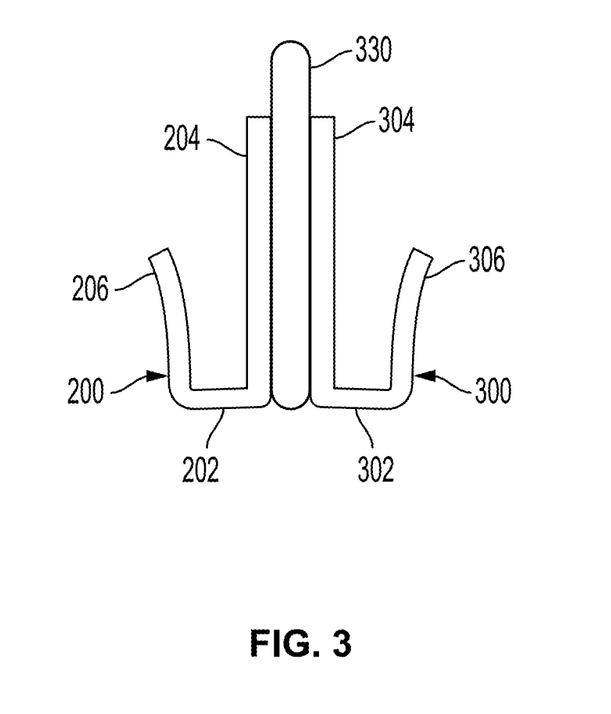
FIG. 3 illustrates a front or anterior view of a pair of septum supports that operate together to maintain an upright position of the septum.

FIG. 3 illustrates a front or anterior view of a pair of septum supports, i.e., the right septum support 200 of FIG. 1 and a left septum support 300, that operate together to maintain an upright position of the septum 330. The left septum support 300 essentially is a mirror image of the right septum support 200 with the septum 330 being the plane of reflection. Similar to the right septum support 200, the left septum support 300 includes a base member 302 configured to be placed on a bottom or floor of the left side of the nasal cavity, a first side member 304 configured to be placed in contact with the left side of the septum 330, and a second side member 306 configured to be placed in contact with the inferior or lower turbinate (not shown in FIG. 3) on the left lateral wall of the nasal cavity. The biased configuration of the respective first side member 204, 304 and the second side member 206, 306 allows pressure to be applied to either side of the septum 330 such that the septum 330 is maintained in an upright and/or straight position by the first side members 204, 304 as the septum 330 heals after the operational procedures.

Figure 4:
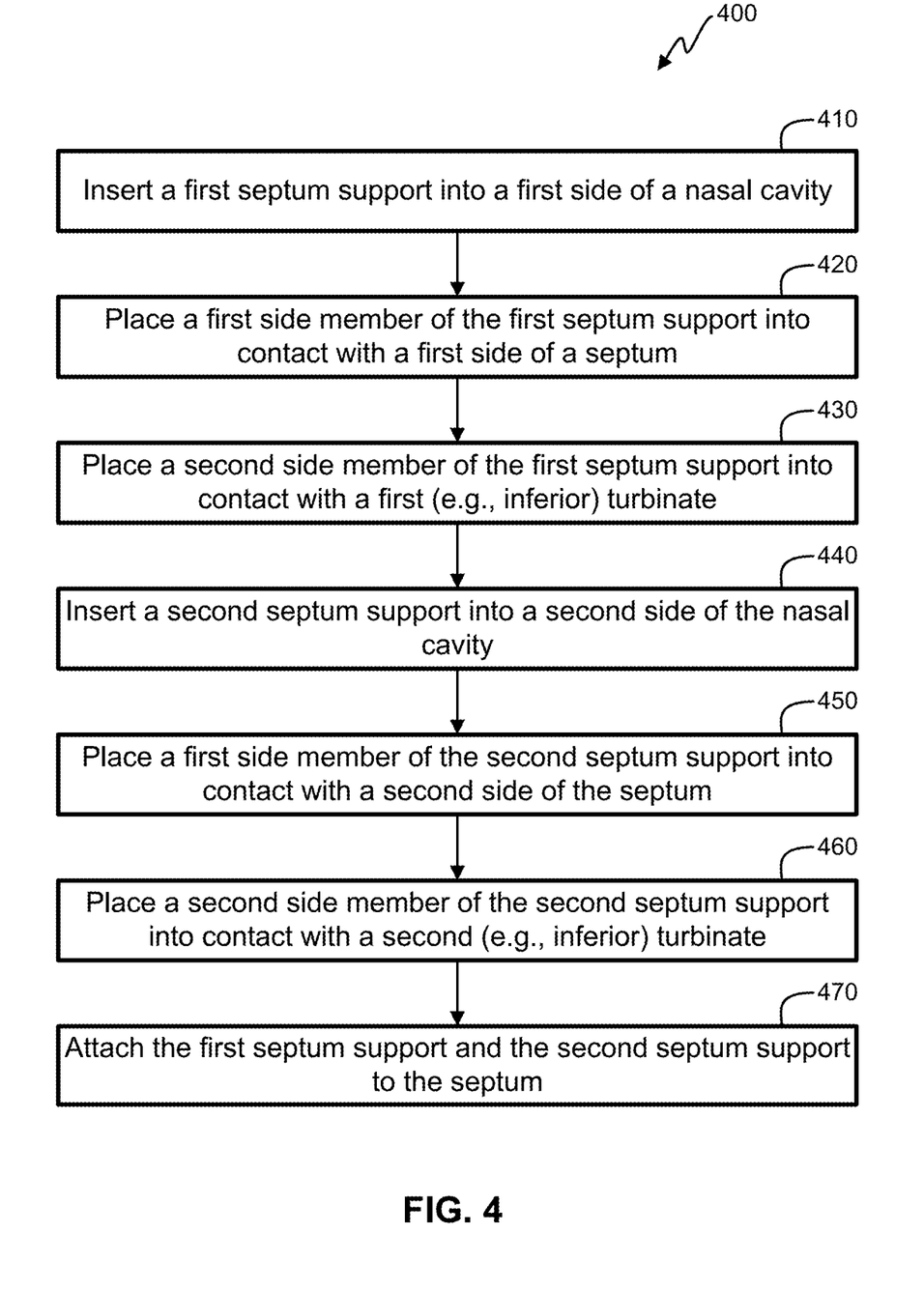
FIG. 4 is a simplified flow chart illustrating a method of using septum supports described herein to create a breathing passage and/or to maintain the position of the septum for a patient.

FIG. 4 is a simplified flow chart 400 illustrating a method of using the septum supports described herein to create a breathing passage and/or to maintain the position of the septum for a patient.

At block 410, a first septum support is inserted into one side of a nasal cavity. The first septum support may be a left or right septum support, similar to the left or right septum support discussed above with reference to FIGS. 2A-2E and 3. The first septum support is resilient or flexible such that the first septum support may be pinched, bended, or folded to facilitate the insertion of the first septum support. In some instances, pressure may be applied to a first side member and a second side member of the first septum support to reduce a distance between the first side member and the second side member to facilitate insertion of the first septum support into the one side of the nasal cavity. Once the first septum support is inserted into the nasal cavity, the pressure may be released from the first side member and the second side member to restore at least a portion of the distance between the first side member and the second side member.

At block 420, the position of the first septum support may be adjusted so as to place the first side member into contact with one side of the septum. At block 430, the second side member is placed into contact with a turbinate, such as the inferior or lower turbinate.

At block 440, a second septum support is inserted into the other side of the nasal cavity. The second septum is a mirror image of the first septum support. Similar to the first septum support, the second septum support is resilient or flexible such that the second septum support may be pinched, bended, or folded to facilitate the insertion of the second septum support into the nasal cavity. For example, pressure may be applied to a first side member and a second side member of the second septum support to reduce a distance between the first side member and the second side member to facilitate insertion of the second septum support into the nasal cavity. Once the second septum support is inserted into the nasal cavity, the pressure may be released from the first side member and the second side member to restore at least a portion of the distance between the first side member and the second side member.

At block 450, the position of the second septum support may be adjusted so as to place the first side member of the second septum support into contact with the other side of the septum. At block 460, the second side member is placed into contact with another turbinate, such as the other inferior or lower turbinate.

As discussed above, the first and second side members are in a biased configuration. Such configuration allows pressure to be applied to either side the septum once the first and second septum supports are placed inside the nasal cavity, maintaining the septum in an upright or straight position.

At block 470, the first septum support and the second septum support are attached to the septum so as to maintain the position of each septum support relative to the septum. The respective first members of the first and second septum supports may each include a suture hole, and a common suture may be applied through both suture holes to secure the first and second septum supports in place. Alternatively, the first and second septum supports may be secured in place via gluing, adhering, or another suitable attaching mechanism.

The following embodiments described are directed to a nasal stent that is positionable within the nose to open up an airway or fluid passage within the nose. The nasal stent may be used to create access for a surgeon to reach sinuses, to access the sphenopalatine ganglion, etc., during operational procedures.

Referring back to FIG. 1, during a surgical procedure, the superior turbinate 102 generally does not impede access to the rear portions of the sinus cavity. The middle turbinate 104, however, impedes access to the sinuses for sinus surgery. In performing surgical procedures, it is desirable to maximize the viewing space for the sinus cavities. In order to gain access to the sinus cavity, the surgeon must displace the middle turbinate 104 from its lateral position to a medial position, typically, against the nasal septum. Conventionally, the surgeon displaces the middle turbinate 104 from its lateral position toward the nasal septum by medially displacing the inferior attachment with a surgical instrument, such as a Freer elevator. Despite this maneuver, the turbinate 104 tends to migrate laterally. The surgeon, then, must add to the initial trauma incurred with medialization of the middle turbinate 104 by repeatedly recompressing the middle turbinate 104 to a medialized position in order to regain view and access to the sinus cavity.

The embodiments of the nasal stent described herein may be used to maintain the medialized position of one of the turbinates, such as the middle turbinate 104. In some embodiments, the nasal stent described herein is positionable on one side, specifically, the lateral side, of one of the turbinates and is able to press against that turbinate medially toward the septum and hold that turbinate in a displaced position, typically against the septum. The displaced turbinate increases the viewing space within the nasal cavity and provides access to portions of the sinus that are typically blocked or covered by the turbinate. The stent is made of a flexible and resilient material that is able to be easily inserted within the nasal cavity and to press and hold the turbinate in the displaced position.

Constant maintenance of the medialized turbinate position allows for a continuous, maximized view of the sinus cavity. By maximizing the viewing area, the surgeon has improved access to the sinuses and improved efficiency while minimizing the likelihood for a surgical complication. Moreover, the nasal stent minimizes trauma to the turbinate caused by repeatedly repositioning the turbinate medially with the Freer elevator, which can cause permanent alteration of the turbinate and affect the turbinate's function. In contrast, the stent described herein is able to displace the turbinate, such as the middle turbinate, with minimization of trauma. Further, the stent eliminates the time requirement for repeated turbinate compressions, which in turn, improves surgeon efficiency and shortens the operation time for the patient. The nasal stent may be sufficiently flexible to enable easy insertion within the nose yet sufficiently stiff or rigid to maintain medial displacement of the turbinate.

Figure 5:
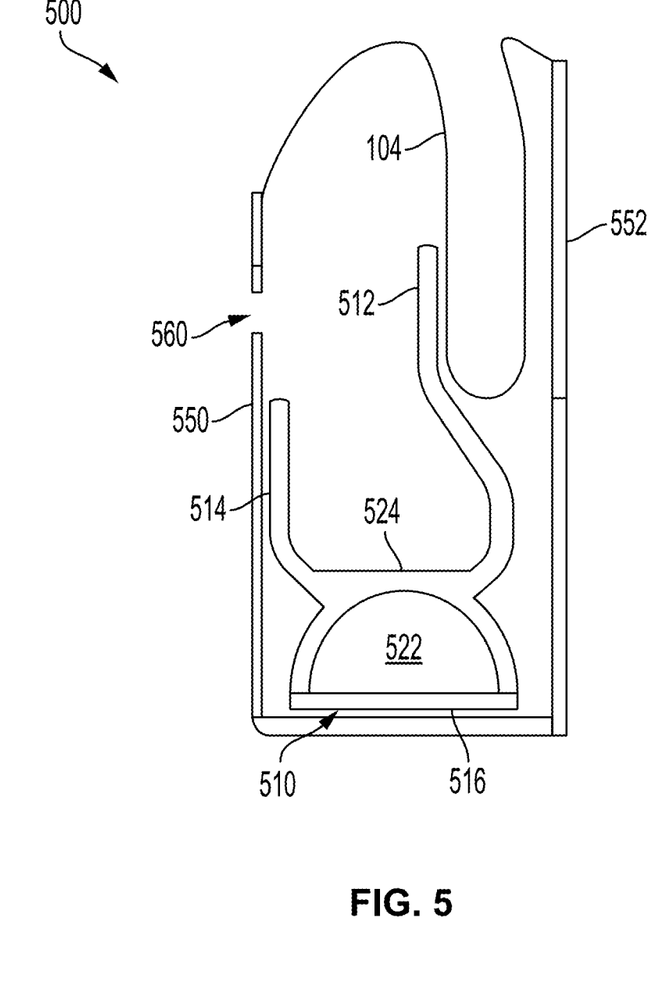
FIG. 5 illustrates a right front or anterior view of the nasal airway with an embodiment of a nasal stent inserted therein.
Figure 6:
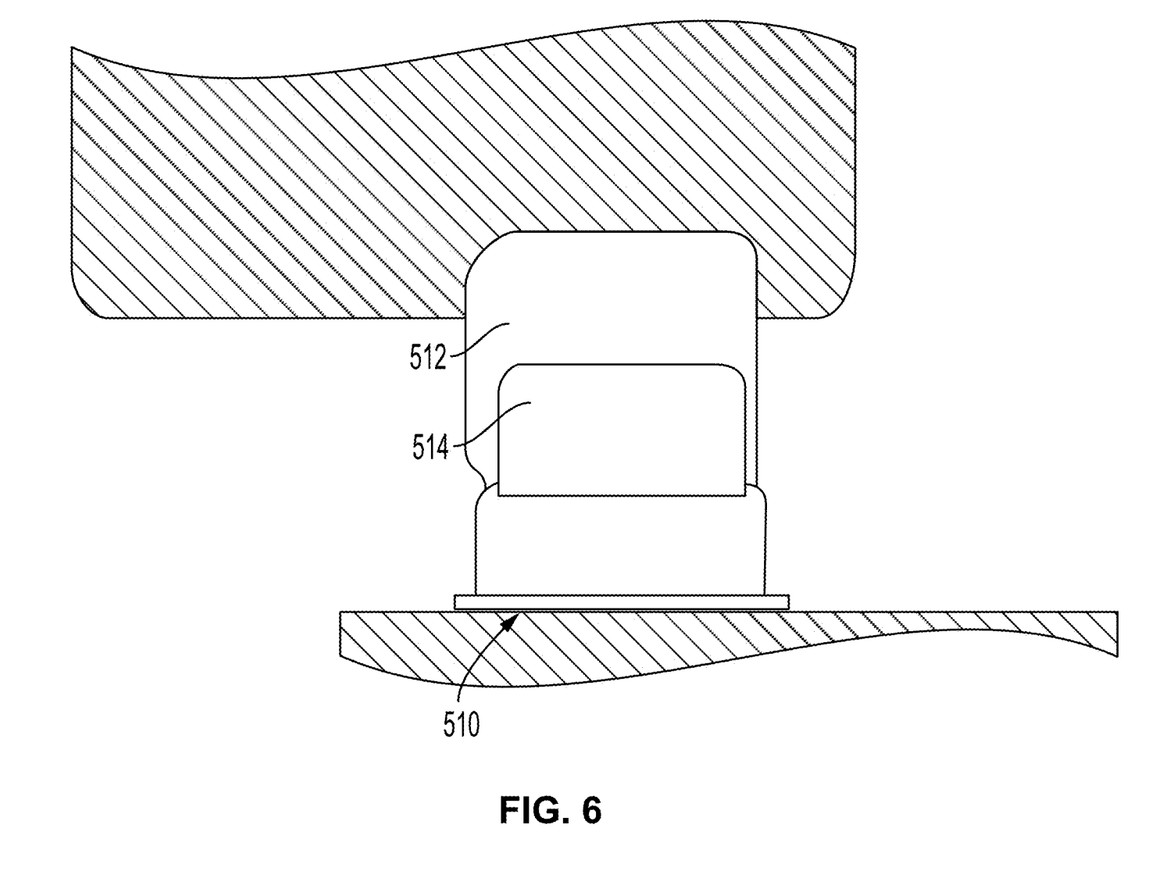
FIG. 6 illustrates a right side or lateral view of the nasal stent of FIG. 5 placed against a turbinate.

FIG. 5 illustrates a right front or anterior view 500 of the nasal airway with a nasal stent 510 inserted therein. FIG. 6 illustrates a right side or lateral view of the nasal stent 510 placed against a turbinate. As shown in FIG. 5, the nasal stent 510 includes a first side member or a medial member 512 that is positionable against a turbinate, such the middle turbinate 104, and a second side member or a lateral member 514 that is positionable against a lateral nasal wall 550 of the nasal cavity. The lateral nasal wall 550 of the nasal cavity supports the second side member 514 as the second side member 514 presses laterally against the wall 550.

Figure 7:
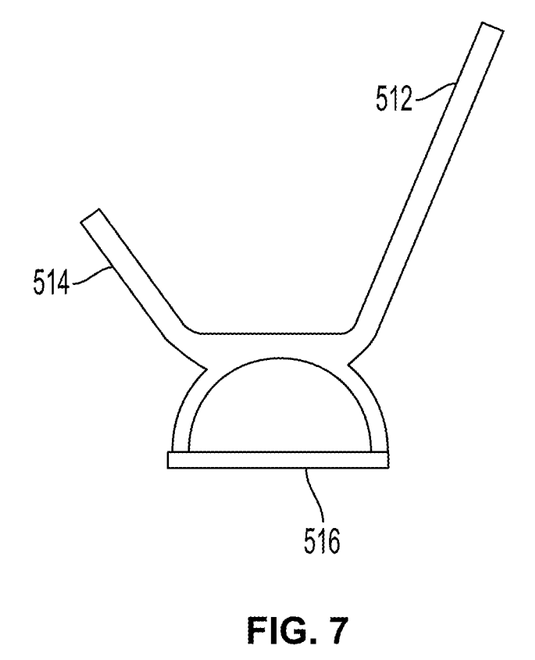
FIG. 7 illustrate another embodiment of a nasal stent.
Figure 8:
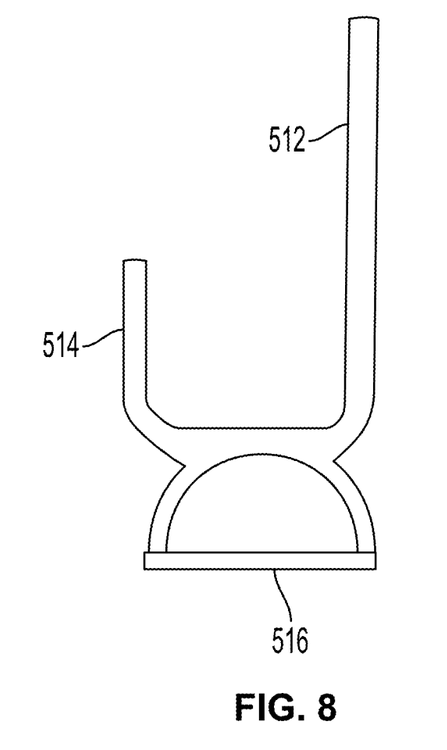
FIG. 8 illustrate a further embodiment of a nasal stent.

The nasal stent 510 is configured so that the first side member 512 and the second side member 514 are biased away from one another, which results in the first side member 512 pressing against the middle turbinate 104, which displaces the middle turbinate 104 medially toward and typically into contact with the septum 552. The first side member 512 and the second side member 514 may be walls that extend upwardly from a base or base member 516 of the stent 510. In some embodiments the first side member 512 and the second side member 514 extend diagonally upward from the base 516 relative to one another so that the first side member 512, the second side member 514, and the base member 516 roughly form or have a V-shaped configuration, such as shown in FIG. 7. The V-shaped configuration aids in biasing the first side member 512 and the second side member 514 away from one another when the nasal stent 510 is positioned within the nasal cavity. In other embodiments, the first side member 512 and the second side member 514 may extend roughly parallel to one another so that the nasal stent 510 has a roughly U-shaped configuration, such as shown in FIG. 8.

The second side member 514 is typically shorter than the first side member 512. The shorter second side member 514 enables the second side member 514 to be positioned against the lateral nasal wall 550 without covering the maxillary sinus ostium 560 (the opening into the sinus behind the cheek). The longer first side member 512 enable the first side member 512 to fully contact and engage the middle turbinate 104 and to press or displace the middle turbinate 104 medially toward and typically into contact with the septum 552. The first side member 512 is typically long enough so that the first side member 512 is positioned at least half way up the middle turbinate 104.

In some embodiment, a reinforcing member may be used with the nasal stent 510. For example, a reinforcing member may be positioned between the first side member 512 and the second side member 514 to help bias the first side member 512 and the second side member 514 apart. The reinforcing member may be a separate component from the nasal stent 510 or may be incorporated within the material body of the nasal stent 510. The reinforcing member is ideally made of a flexible or elastic material that is rigid enough to properly reposition and support the middle turbinate 104. In a specific embodiment, the reinforcing material is made of Nitinol, silicone, or a polymer material. The reinforcing material may be molded into the material body of the nasal stent 510 (e.g., via insert molding) or may be positioned about the nasal stent 510 in a manner that biases the first side member 512 and the second side member 514 apart. In the latter instance, the nasal stent 510 may be designed or configured to accommodate the separate reinforcing material, such as by including grooves or other features that couple with the reinforcing member. In other embodiments, the reinforcement may be achieved by using different materials within the stent, such as a rigid base member and flexible or elastic walls.

The nasal stent 510 herein minimizes trauma to the middle turbinate 104 caused by repeatedly repositioning the middle turbinate 104 medially with an instrument, such as a Freer elevator. The nasal stent 510 thus allows the surgeon improved efficiency and less operating time for the patient. The nasal stent 510 is also able to maintain displacement of the middle turbinate 104 with minimized trauma.

The use of the stent may help maintain the surgical displacement of the turbinate by between about 1 mm and about 15 mm, between about 3 mm and about 12 mm, and more commonly between about 5 mm and about 10 mm, in comparison with an original position/orientation of the turbinate within the nasal cavity.

With further reference to FIG. 5, in some embodiments, the nasal stent 510 includes a lumen or half pipe 522 near the base 516 of the nasal stent 510. The lumen 522 may be formed by connecting first side member 512 and the second side member 514 of the nasal stent 510 upward from the base 516. The lumen 522 enables a surgical instrument, such as a suction device to be inserted through the nasal cavity and into or adjacent the rear sinus. The connection wall 524 that forms the lumen 522 may also reinforce the nasal stent 510 and increase the rigidity of the nasal stent 510 to prevent the first side member 512 and the second side member 514 from collapsing inward and into contact. The lumen 522 may also enable the physician to access the sphenopalatine ganglion, which is the main nerve branch of the sinus area and back of the nose. Accessing the sphenopalatine ganglion may allow a physician to numb the nerves in the back of the nose and sinus area, which may reduce the discomfort that a patient experiences in the surgical procedure.

The nasal stent 510 is inserted in the nasal cavity with the base 516 angled in comparison to its final position. In some embodiment, the nasal stent 510 may be inserted in a roughly perpendicular orientation to its final position. During insertion, the nasal stent 510 is relatively narrow because it is made of a flexible material. The lumen 522 may be collapsed using a pair of forceps or another instrument that may put pressure on the nasal stent 510. Once the nasal stent 510 is in position, it may be rotated into its final position.

In some embodiments, the lumen may be removed so that the nasal stent is a more U-Shaped or V-shaped component. The alternative embodiment may enable easier insertion of the nasal stent since the connection wall or bridge does not resist compression or folding of the first side member and the second side member during insertion. The U or V-shaped stent may more easily accommodate unique configurations of the nasal cavity, such as by allowing the first second side member and the second side member to bend, flex, or displace around features of the nasal cavity.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A device for creating a breathing passage and for maintaining a position of a septum of a patient, the device comprising:
    a base member, the base member having a width defined between a first edge of the base member and a second edge of the base member;
    a first side member extending vertically upward from the first edge of the base member, the first side member being made of a flexible material and being configured to contact a septum of a nasal cavity; and
    a second side member extending upward away from the second edge of the base member to an upper edge of the second side member, the second side member also being made of the flexible material and having a single curved portion from the second edge of the base member to the upper edge of the second side member with a convex surface facing the first side member and a concave surface opposite the convex surface, the concave surface being configured to distribute pressure uniformly when in contact with an inferior turbinate, wherein the first side member and the second side member diverge from the base member such that at a vertical position above the base member, a distance between the first side member and the second side member is greater than the base member width.

2. The device of claim 1, wherein an upper edge of the first side member is further from the base member than the upper edge of the second side member.

3. The device of claim 1, wherein the base member, the first side member, and the second side member define a U shape with a substantially flat inner bottom and uneven sides.

4. The device of claim 1, wherein at least one of the first side member or the second side member comprises a shape memory alloy, a superelastic alloy, an elastic material, or a polymer.

5. The device of claim 1, wherein at least one of the first side member or the second side member comprises Nitinol or silicone.

6. The device of claim 1, wherein the base member is bendable or foldable to facilitate insertion of the device into a nasal cavity.

7. The device of claim 1, further comprising a reinforcing member at least partially embedded in at least one of the first side member or the second side member such that the reinforcing member biases the first side member and the second side member apart.

8. The device of claim 1, further comprising a reinforcing member positionable between the first side member and the second side member such that the first side member and the second side member are biased away from one another.

9. The device of claim 8, wherein at least one of the first side member or the second side member comprises grooves configured to engage the reinforcing member.

10. The device of claim 1, wherein the first side member comprises an aperture for securing the device to the septum via suturing.

11. The device of claim 1, wherein the second side member includes a length defined by a proximal edge of the second side member and a distal edge of the second side member such that the second side member is configured to extend longitudinally along and maintain contact with a portion of the inferior turbinate while at least preventing blockage of sinuses or limiting contact with a middle turbinate above, and wherein the length of the second side member is less than a length of the first side member.

12. The device of claim 11, wherein the length of the second side member ranges between about 35 mm and about 45 mm and the length of the first side member ranges between about 65 mm and about 75 mm.

13. The device of claim 11, wherein the base member has a length that is substantially the same as the length of the first side member.

14. The device of claim 1, wherein the second side member includes a height defined by the upper edge of the second side member and the second edge of the base member such that the second side member is configured to extend vertically along and maintain contact with a portion of the inferior turbinate while avoiding contact with a middle turbinate, and wherein the height of the second side member is less than a height of the first side member.

15. The device of claim 14, wherein the height of the second side member ranges between about 5 mm and about 15 mm and the height of the first side member ranges between about 15 mm and about 25 mm.

16. The device of claim 1, wherein a thickness of the base member is greater than at least one of a thickness of the first side member or a thickness of the second side member.

17. The device of claim 1, further comprising a connecting member that connects the first side member and the second side member such that a lumen is formed near the base member that provides nasal access for a medical device.

18. The device of claim 1, wherein the base member is substantially planar, the base member being configured to rest on a bottom or floor of a patient's nasal cavity.

19. The device of claim 1, wherein the distance between the first side member and the second side member increases as the second side member extends upward from the second edge of the base member to the upper edge of the second side member.

20. The device of claim 1, wherein the distance between the first side member and the second side member at the upper edge of the second side member is greater than the base member width.

* * * * *